United States Patent
Lenker

(10) Patent No.: US 7,695,452 B2
(45) Date of Patent: *Apr. 13, 2010

(54) METHOD AND APPARATUS FOR VENOUS DRAINAGE AND RETROGRADE CORONARY PERFUSION

(75) Inventor: Jay A. Lenker, Laguna Beach, CA (US)

(73) Assignee: Indian Wells Medical, Inc., Laguna Beach, CA (US)

( * ) Notice: Subject to any disclaimer, the term of this patent is extended or adjusted under 35 U.S.C. 154(b) by 1379 days.

This patent is subject to a terminal disclaimer.

(21) Appl. No.: 10/997,739

(22) Filed: Nov. 23, 2004

(65) Prior Publication Data

US 2005/0113799 A1 May 26, 2005

Related U.S. Application Data

(63) Continuation of application No. 10/759,310, filed on Jan. 16, 2004, now Pat. No. 6,821,263, which is a continuation-in-part of application No. 09/894,564, filed on Jun. 28, 2001, now Pat. No. 6,682,499.

(51) Int. Cl.
*A61M 29/00* (2006.01)
*A61M 31/00* (2006.01)
*A61M 37/00* (2006.01)

(52) U.S. Cl. .............. 604/96.01; 604/508; 604/103.05

(58) Field of Classification Search .............. 604/96.01, 604/101.03–101.05, 102.01, 102.03, 103.1, 604/164.01, 533–535, 103.03, 103.05, 103.06, 604/103.07, 500, 503, 508, 509, 93.01, 4.01; 606/192, 194

See application file for complete search history.

(56) References Cited

U.S. PATENT DOCUMENTS

| 4,943,277 | A | * | 7/1990 | Bolling | 604/101.03 |
|---|---|---|---|---|---|
| 6,099,498 | A | * | 8/2000 | Addis | 604/96.01 |
| 6,682,499 | B2 | * | 1/2004 | Lenker | 604/4.01 |
| 6,726,651 | B1 | * | 4/2004 | Robinson et al. | 604/101.01 |
| 6,821,263 | B2 | * | 11/2004 | Lenker et al. | 604/4.01 |

* cited by examiner

*Primary Examiner*—Matthew F Desanto

(57) ABSTRACT

A system is disclosed for cannulating the vena cava of a patient during cardiopulmonary bypass procedures. Such cannulation is necessary for drainage of venous blood from the patient so that it may be oxygenated and pumped back to the patient to perfuse tissues during cardiac surgery and, more specifically, during periods of ischemic cardiac arrest or dysfunction. The device of the present invention not only provides venous drainage for cardiopulmonary bypass, but also performs the function of routing cardioplegic solution through the heart in the retrograde direction. Such cardioplegia provides protection to the heart during periods of ischemic cardiac arrest. This invention replaces a plurality of cannulae currently used for open-heart surgery, thus simplifying the surgical field and improving visibility of the heart. The device allows for the delivery of retrograde cardioplegia to the coronary circulation of both the right and the left side of the heart. The device further includes protection mechanisms to prevent overinflation or excessive pressurization of the right atrium during retrograde delivery of cardioplegia solution.

19 Claims, 11 Drawing Sheets

METHOD AND APPARATUS FOR VENOUS DRAINAGE AND RETROGRADE CORONARY PERFUSION

PRIORITY CLAIM

This application is a continuation of U.S. application Ser. No. 10/759,310, now U.S. Pat. No. 6,821,263, filed Jan. 16, 2004, which is a continuation-in-part of U.S. application Ser. No. 09/894,564, now U.S. Pat. No. 6,682,499, filed on Jun. 28, 2001, the entirety of which are hereby incorporated herein by reference.

FIELD OF THE INVENTION

The field of this invention is cardiac bypass surgery and cardiopulmonary bypass.

BACKGROUND OF THE INVENTION

During cardiac surgery for procedures such as coronary artery bypass grafting, heart valve repair or replacement, septal defect repair, pulmonary thrombectomy, atherectomy, aneurysm repair, aortic dissection repair and correction of congenital defects, cardiopulmonary bypass and cold cardiac ischemic arrest are often required. Typically, a cooled cardioplegia solution, a solution containing elevated levels of potassium, for example, is administered in the antegrade direction (in the direction of normal blood flow) through the patient's aorta and into the coronary arteries. The cold (2 to 3 degrees centigrade) cardioplegia solution stops the heart from beating and reduces its temperature to minimize damage to the heart during surgery. The cardioplegia solution exits the coronary circulation through the coronary veins at the coronary sinus, where it empties into the right atrium. Cardiopulmonary bypass maintains the peripheral circulation of oxygenated blood to all body organs except the heart during the period of cold, cardioplegic, ischemic arrest.

For some patients, such as those suffering from critical coronary artery stenosis and aortic valve disease, antegrade perfusion may be difficult, inefficient and incomplete. Retrograde (in the direction opposite of normal blood flow) cardioplegia, using current technology, may be administered via the coronary sinus into the coronary circulation using devices, which cannulate the coronary sinus. Such cannulation of the coronary sinus by prior art devices requires inserting a catheter into the coronary sinus and perfusing cardioplegia into the sinus. Drainage of cardioplegia solution is accomplished into the coronary ostea located at the base of the aorta. The problem with prior art methods is that either the right or left heart will be perfused, but not both, since the right coronary veins come off the coronary sinus at an angle and are not cannulated by current catheters that cannulate the left coronary veins. Thus, incomplete perfusion of segments of the heart muscle, primarily the right heart and septum, will occur since the right coronary veins frequently come off near the coronary sinus ostea or within the right atrial wall proper. The right coronary veins are not perfused by prior art retrograde cardioplegic catheters.

Currently surgeons performing cardiac bypass surgery use one or more cannulae for venous drainage and an additional cannula for retrograde perfusion. The multiple cannulae are obstacles and restrict visibility in the surgical arena. Placement of the cardioplegia cannula into the coronary sinus is a semi-blind procedure performed through an additional purse-string suture-closed access port via the right atrium. The retrograde cannula may be improperly positioned within the coronary sinus, which results in critical coronary vessels being inadequately perfused. Typically, placement of currently available retrograde cardioplegia cannula within the coronary sinus results in retrograde perfusion of the left heart but inadequate retrograde perfusion of the right heart because of cannula obstruction of the right coronary ostea as they arise from the coronary sinus. Thus the tissue of the left heart is perfused, in a retrograde direction, with cardioplegia solution but the right heart is perfused with a diminished, or no, supply of cardioplegia solution since the right coronary veins are generally a side-branch of the left coronary veins at the coronary sinus and the right coronary veins are blocked by the cannula. Poor right heart retrograde perfusion occurs because, most-frequently, anatomic variations of the right coronary sinus and veins cannot be properly perfused with the currently available cannula.

New devices and methods are needed, which facilitate cold cardioplegic arrest, yet limit the number of cannulae required to isolate the heart and coronary blood vessels from the peripheral vasculature, arrest the heart, protect all the coronary blood vessels, protect all or most of the myocardium, and drain venous blood from the inferior and superior vena cava. Furthermore, it would be advantageous to the diseased myocardium being subjected to ischemic arrest if a retrograde cardioplegia perfusion cannula could perfuse the coronary vasculature of both the right and left heart simultaneously.

SUMMARY OF THE INVENTION

This invention relates to a balloon, or tourniqueted, catheter or cannula useful in the retrograde administration of cardioplegia through the coronary sinus and simultaneous venous drainage during cardiac bypass surgery without the need to cannulate the coronary sinus.

The invention is a cannula for performing venous drainage and retrograde perfusion of the heart during cardiac bypass surgery. A single multi-lumen cannula of the present invention can perform the same function as multiple cannulae currently used. The cannula of the invention for cardioplegic administration can improve the protection of a heart during periods of ischemia such as occurs during open-heart surgery. The cannula is preferably fabricated from materials, which are biocompatible for the intended use.

One embodiment of the invention is a multi-lumen cannula with occlusive structures for the superior and inferior vena cava, a protection structure, cardioplegia infusion channel, a pressure monitoring port, and venous drainage ports. Occlusion structures may include devices such as, but not limited to, balloons, umbrellas, structures that draw a vacuum against a wall of the heart, externally applied tourniquets, umbrellas with rim-seal balloons, or the like. In a preferred embodiment, the occlusion structures are balloons constructed of elastomeric materials or vacuum-assisted walled structures.

In one embodiment, a first lumen of the cannula is connected to the cardioplegia infusion system and provides cardioplegia solution to arrest the heart. A second cannula lumen is connected to the venous drainage system. The drainage ports are located in the second lumen. A third lumen is connected to the balloon inflation system, which provides inflation fluids, such as water, isotonic saline or cardioplegia solution, under controlled pressure or volume to inflate the occlusion balloons. The pressure of the occlusion balloons and right atrium may also be monitored through additional lumens. The occlusion balloons isolate the heart from the peripheral vasculature by occluding the inferior and superior vena cava just proximal to the right atrium. The inferior and superior vena cava balloons utilized to direct flow into the extracorporeal circuit are optionally movable to accommodate anatomic variability. Additional lumens may be utilized for inflation of multiple balloons, pressure monitoring, flow monitoring, drainage of cardioplegia, fluid and drug infusion and the like. Since it is useful to measure cardioplegic perfusion pressure, a pressure transducer or pressure measuring lumen may, for example, be provided at or near the distal end of the cardioplegia perfusion lumen for this purpose.

The cannula may be placed into the vena cava, for example, via a route through the internal jugular vein, cranial vena cava, femoral vein, or brachial vein. A smaller diameter cannula may be placed through any of the smaller venous access ports. The use of smaller venous access ports may be enabled by use of a pump or vacuum powered venous drainage system, typically external to the cannula. In one embodiment, the catheter or cannula combines the functions of several catheters currently used in cardiac surgery. A single catheter, rather than multiple catheters, facilitates the surgery and improves the surgical field because extra cannulae do not obstruct the operative field. In addition, the number of individual catheters is reduced, providing a more cost effective method for cardiac surgery. Most importantly, improved cardiac protection is achieved compared to that of standard retrograde perfusion cannulae.

In yet another embodiment, a single-function venous drainage cannula comprising occlusion balloons, a cannula, a drainage lumen and ports, and a balloon inflation lumen and ports is provided for access through any percutaneous access point and is routed to the right atrium through the venous system. This embodiment would be very useful for emergency cardiac assist.

The cannula of the present invention provides for venous drainage and simultaneous retrograde cardioplegia delivery into the coronary sinus of the heart so that the myocardium of both the right and left heart is perfused. In doing so, the coronary sinus is pressurized. Optionally, some or all of the right atrium is pressurized. Since such pressurization is unnatural for the thin walls of the right atrium, the catheter or cannula, in one embodiment, provides structures that protect the walls of the right atrium from the high perfusion pressures and minimize the risk of wall rupture. These protective structures include double wall balloons that inflate to approximate the interior of the right atrium. The space between the inner wall and the outer wall is ribbed or channeled so that gaps are maintained when a vacuum is drawn in the space between the outer wall and the inner wall of the balloon. The vacuum is drawn through the cannula by a vacuum applied at the proximal end of the cannula by way of a connector. The venous drainage cannula runs through the center of the balloon and allows for venous blood drainage from both the superior and inferior vena cava. The balloon further comprises a walled off region that is disposed laterally relative to the venous drainage cannula and permits pressurization of the coronary sinus with cardioplegia solution which is introduced at the proximal end of the cannula and which flows through a lumen in the cannula to reach the walled-off region. In one embodiment, the protection structure eliminates the need for the occlusive balloons in the vena cava.

In yet another embodiment, the balloon does not require pulling a vacuum but simply inflates to seal off or isolate the walls of the vena cava relative to the walled-off region in which pressurized cardioplegia solution is infused. Seals or gaskets are provided to ensure that such pressure seal is optimized. In yet another embodiment, the vacuum system further comprises an external collection reservoir and plumbing that returns any blood or bodily fluids captured by the vacuum system, to the external cardiopulmonary circuit.

Since the cardioplegia cannula does not cannulate the coronary sinus, it will perfuse both the left and right side of the heart. Perfusion of the right heart may be very important in obtaining optimal patient outcomes following cardiopulmonary bypass. In addition, cold cardioplegic solution will bathe the endomyocardium of the right ventricle aiding in myocardial protection of the right heart.

In one embodiment, a venous cannula is adapted for retrograde administration of cardioplegia solution to a heart and simultaneous venous drainage from a vena cava during cardiopulmonary bypass comprising a cardioplegia solution infusion mechanism, wherein the cardioplegia solution infusion mechanism receives pressurized cardioplegia solution and routes the pressurized cardioplegia solution into a coronary sinus, located in a right atrium of a heart, without cannulating the coronary sinus. The venous cannula further comprises a venous blood drainage mechanism, wherein the venous blood drainage mechanism drains venous blood from a superior and an inferior vena cava. The cannula further comprises a vena cava occlusion mechanism, wherein the vena cava occlusion mechanism occludes the vena cava from the right atrium to prevent pressurized cardioplegia solution from entering the vena cava. The venous cannula further comprises a protection device, wherein the protection device limits pressurization of the right atrium by the pressurized cardioplegia solution.

One aspect of the invention is a method of cannulating a patient's heart during cardiopulmonary bypass comprising the steps of inserting a cannula into a venous system of a patient and then positioning the cannula so that said cannula traverses a right atrium and extends into both a superior and an inferior vena cava. The method further comprises enabling an occlusion device in each of the superior and inferior vena cava and draining venous blood from the vena cava. The method further comprises inflating a protection balloon within the right atrium and infusing cardioplegia solution, in the retrograde direction, into a coronary sinus of the heart, without cannulating the coronary sinus, wherein the cardioplegia solution is infused through the cannula into the coronary sinus.

In another embodiment of the invention, a venous cannula is adapted for retrograde administration of cardioplegia solution to a heart during cardiopulmonary bypass and comprises a length of axially elongate multi-lumen tubing with a proximal end and a distal end, wherein at least one of the lumens is a cardioplegia solution infusion lumen, and a cardioplegia solution infusion annulus located near the distal end of the multi-lumen tubing the infusion annulus being operably connected to the cardioplegia solution infusion lumen. The venous cannula further comprises an annular seal ring surrounding the cardioplegia solution infusion annulus, wherein a vacuum lumen in the multi-lumen tubing is operably connected to the annular seal ring. The venous cannula also comprises a cardioplegia solution infusion mechanism, wherein the cardioplegia solution infusion mechanism receives pressurized cardioplegia solution from an external cardioplegia solution infusion source and delivers it to the cardioplegia solution infusion lumen.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE INVENTION

As used herein the terms distal and proximal are used to clarify the location of various points along the axial length of the venous drainage and retrograde perfusion catheter or cannula. Points are defined with respect to the end grasped by the user and the end that is inserted in the patient in the same manner as would one skilled in the art of medical device catheter construction. The proximal end of the catheter or cannula is defined as that end closest to the user or operator of the catheter or cannula while the distal end of the catheter or cannula is defined as that end that is inserted into the patient.

Figure 1:
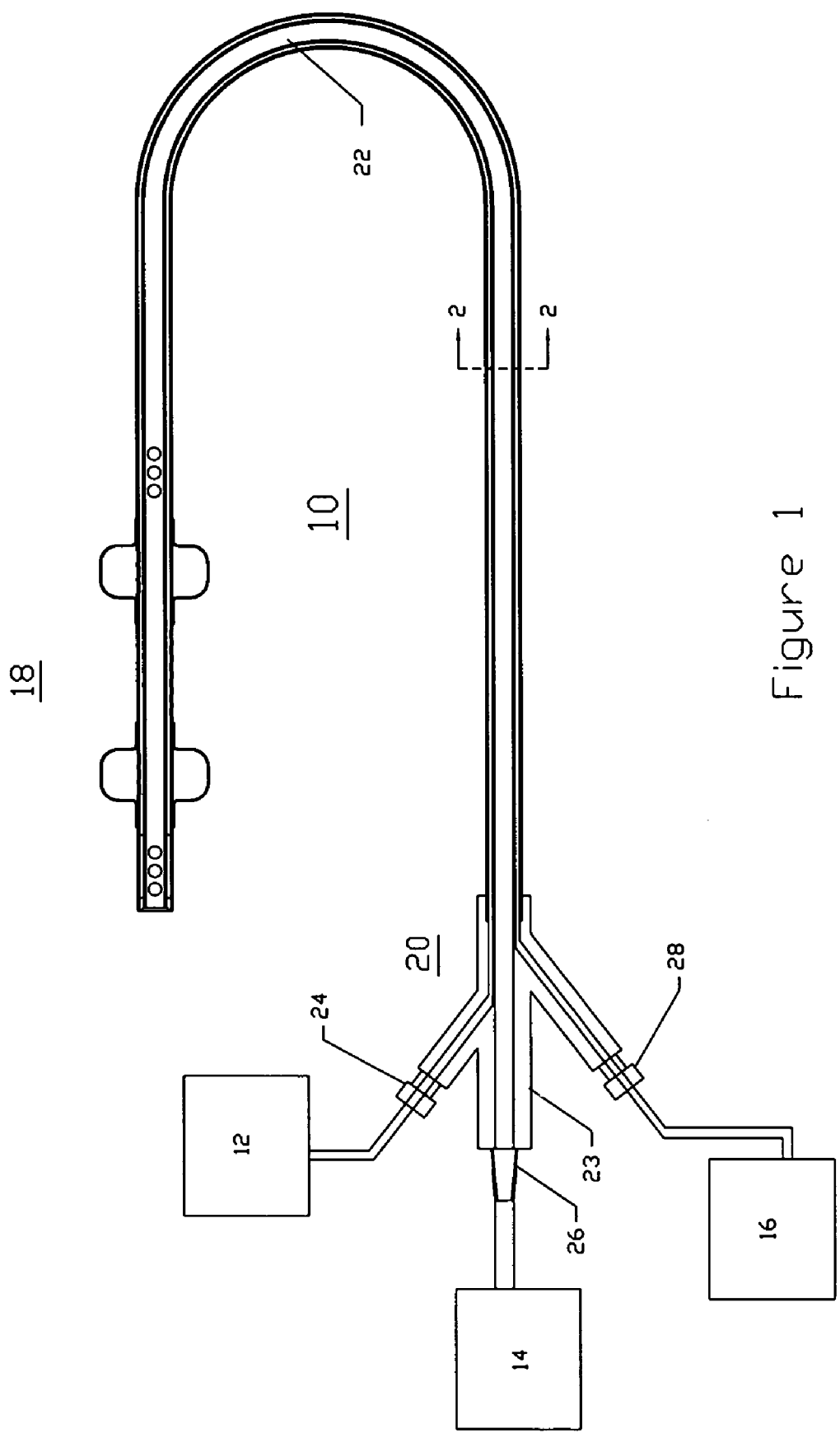
FIG. 1 illustrates a longitudinal cross-section of the cannula of the present invention comprising a distal tip, a proximal end, and a connecting tube according to aspects of an embodiment of the invention. External systems provide for venous drainage, cardioplegia infusion, and balloon inflation.

FIG. 1 illustrates a catheter, tube or cannula 10 of an embodiment of the invention connected to a cardioplegia infusion system or set 12, a venous drainage collection system 14 and an occlusion enabling system 16. In this preferred embodiment, the occlusion enabling system 16 is a balloon inflation system. The catheter 10 comprises a distal tip 18, a proximal end 20, and a length of multi-lumen connection tubing 22. The proximal end 20 comprises a manifold or hub 23. The manifold 23 comprises a cardioplegia infusion adapter or fitting 24, a venous drainage collection adapter or fitting 26, and an occlusion adapter 28. In a preferred embodiment, the occlusion adapter 28 may be a balloon inflation adapter, quick-connect, bayonet, luer fitting, or the like. The manifold 23 is typically molded from materials such as, but not limited to, polymers such as polyvinyl chloride, polycarbonate, ABS, polyimide, poly methyl-methacrylate, or the like.

The cardioplegia infusion adapter 24 is connected to the cardioplegia infusion system 12. The cardioplegia infusion adapter 24 may be any fluid-tight fitting, such as, for example, a luer adapter, quick-connect, or other fluid-tight fitting, suitable for use with the cardioplegia infusion set 12. The standard cardioplegia system 12 generally comprises a pressurized or non-pressurized bag of cardioplegia solution, a roller pump or similar pressurizing system, a length of tubing and a plurality of connectors. Standard cardioplegia solutions include those comprising water, electrolytes such as but not limited to potassium, crystalloid solutions, blood, and the like.

The venous drainage collection adapter 26 is connected to the venous drainage collection system 14. The drainage collection adapter 26 is typically larger in diameter than the balloon inflation fitting 28 or cardioplegia infusion fitting 24. The drainage collection adapter 26 should be capable of being connected to the gravity fed, pump driven or vacuum fed drainage system 14 and is, for example, a ⅜ inch to ½ inch diameter hose barb but could be as small as ⅛ inch in diameter. Standard venous drainage systems 14 generally comprise a connector, a length of tubing and a venous reservoir. Optionally, a vacuum pump may be connected to the venous reservoir.

The balloon inflation adapter 28 is connected to the balloon inflation system 16. The balloon inflation adapter 28 is typically a female luer fitting but may be any fluid-tight fitting suitable for use with an inflation syringe or the like. The standard balloon inflation system 16 comprises a syringe, a volume of balloon inflation fluid such as saline or radiopaque media, and a valve or stopcock associated with each balloon inflation adapter 28. Additionally, the balloon inflation system 16 could comprise a device, such as, for example, a jackscrew, which is a threaded rod moved longitudinally by a longitudinally affixed but rotatable nut, or a pressurized hydraulic cylinder, to advance or withdraw a plunger on the syringe using mechanical advantage.

Figure 2:
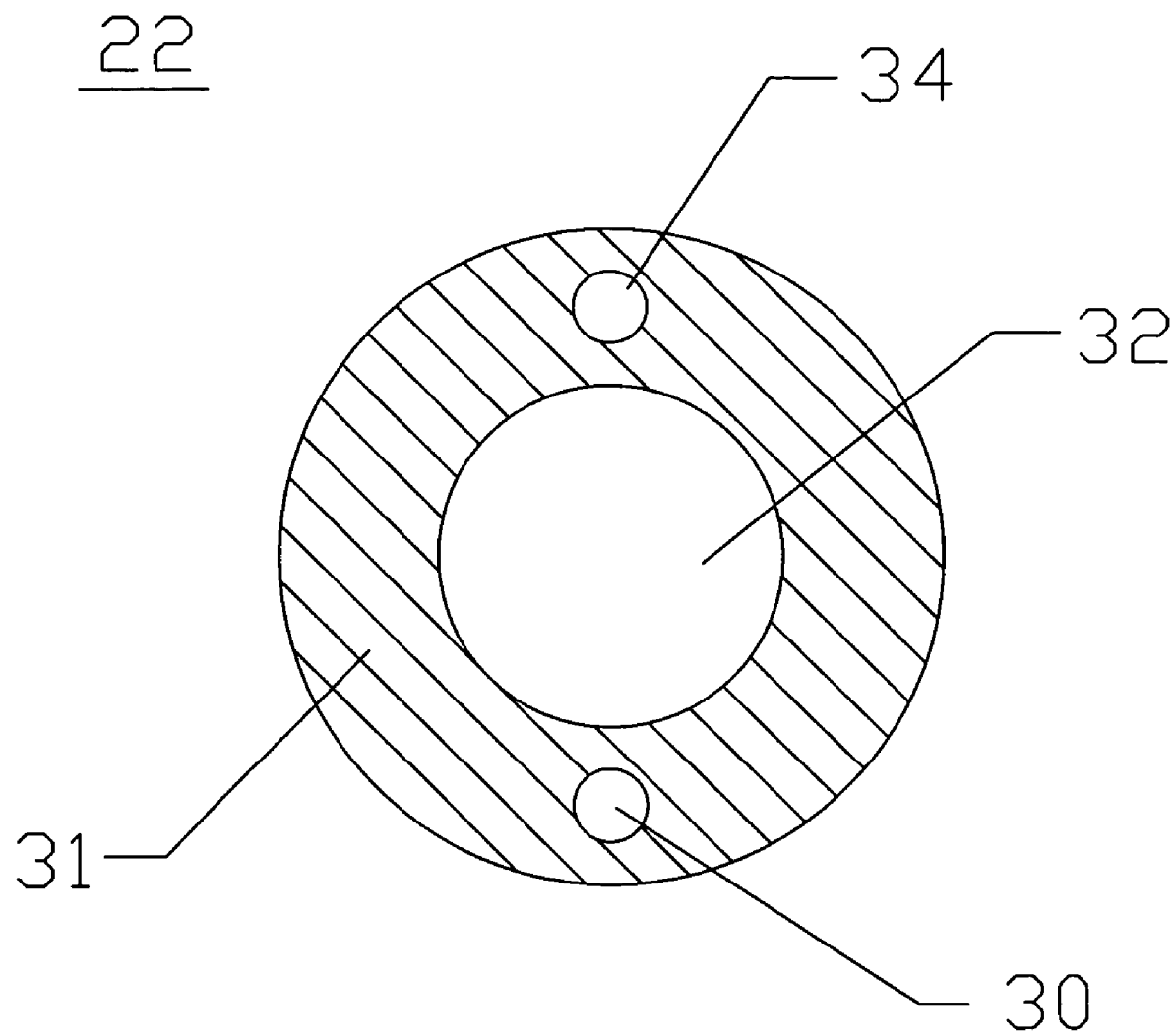
FIG. 2 illustrates a lateral cross-section of a multi-lumen axially elongate tube for construction of the cannula according to aspects of an embodiment of the invention.

FIG. 2 shows the cross-section of the connection tubing 22. The connection tubing 22 may be a length of multi-lumen tubing comprising an infusion lumen 30, a venous drainage lumen 32, an inflation lumen 34, and a wall 31. The connection tubing 22 is preferably made from a polymeric material such as polyvinyl chloride, polyethylene, polypropylene, polyurethane and the like. In a preferred embodiment, the tubing 22 is transparent.

Figure 3:
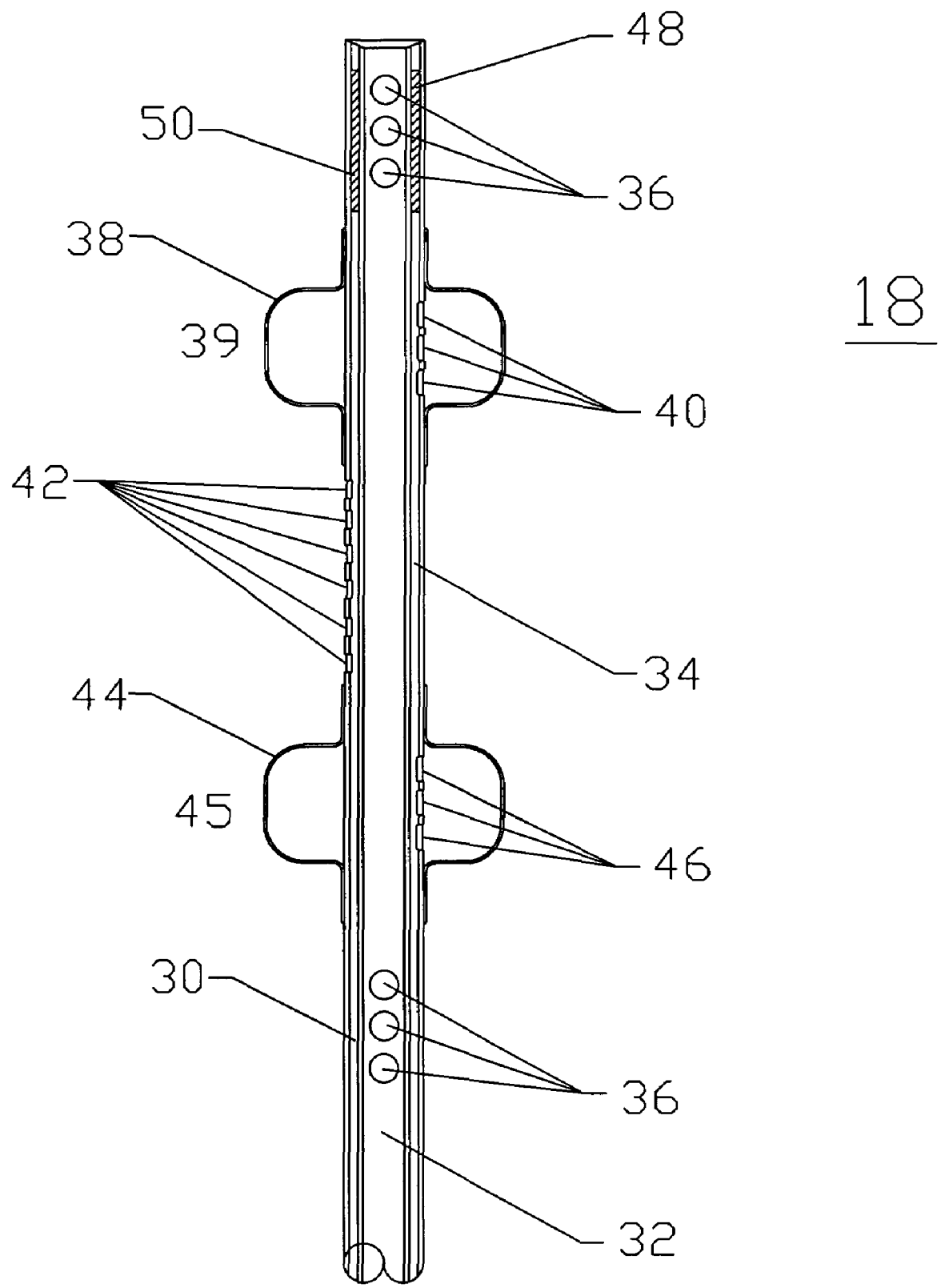
FIG. 3 illustrates, in detail, a longitudinal cross-section of the distal tip of the cannula of FIG. 1 according to aspects of an embodiment of the invention.

FIG. 3 illustrates the distal tip 18 of the catheter 10 of FIG. 1 in detail. The distal tip 18 is an extension of the connecting tubing 22 and comprises the infusion lumen 30, the venous drainage lumen 32 and the inflation lumen 34. Additionally, the distal tip 18 comprises a plurality of venous drainage ports 36, a distal or first occlusion device 39, a plurality of cardioplegia infusion port or ports 42, and a proximal or second occlusion device 45. The distal tip 18 further comprises an inflation lumen plug 48 and an infusion lumen plug 50. A cardioplegic drainage lumen may likewise be utilized to adjust cardioplegic perfusion pressures, if needed.

In an embodiment, the first occlusion device 39 comprises a first balloon 38 and a plurality of first balloon inflation ports 40. The second occlusion device 45 comprises a second balloon 44 and a plurality of second balloon inflation ports 46.

The venous drainage ports 36 are openings in the drainage lumen 32 and connect the venous drainage lumen 32 with the exterior of the cannula 10. There is no communication between the venous drainage lumen 32 and the other cannula lumens 30 and 34. The venous drainage ports 36 are preferably located more proximally than the second balloon 44 and/or more distally than the first balloon 38 on the cannula 10.

The balloon inflation ports 40 and 46 are located on the inflation lumen 34. The inflation lumen 34 is isolated from the other cannula lumens 30 and 32. The first balloon 38 and the second balloon 44 are located over the first balloon inflation ports 40 and the second balloon inflation ports 46, respectively. When the balloon inflation fluid flows through the inflation ports 40 and 46 from the inflation lumen 34, the balloons 38 and 44 inflate.

The cardioplegia infusion port(s) 42 are openings on the infusion lumen 30. The infusion lumen 30 is isolated from the other lumens 32 and 34. The cardioplegia infusion ports 42 are located between the balloons 38 and 44 such that cardioplegia solution is infused between the balloons 38 and 44 and is directed into the right atrium and ventricle of the heart where it subsequently passes into the coronary arteries by way of the coronary sinus.

Figure 4:
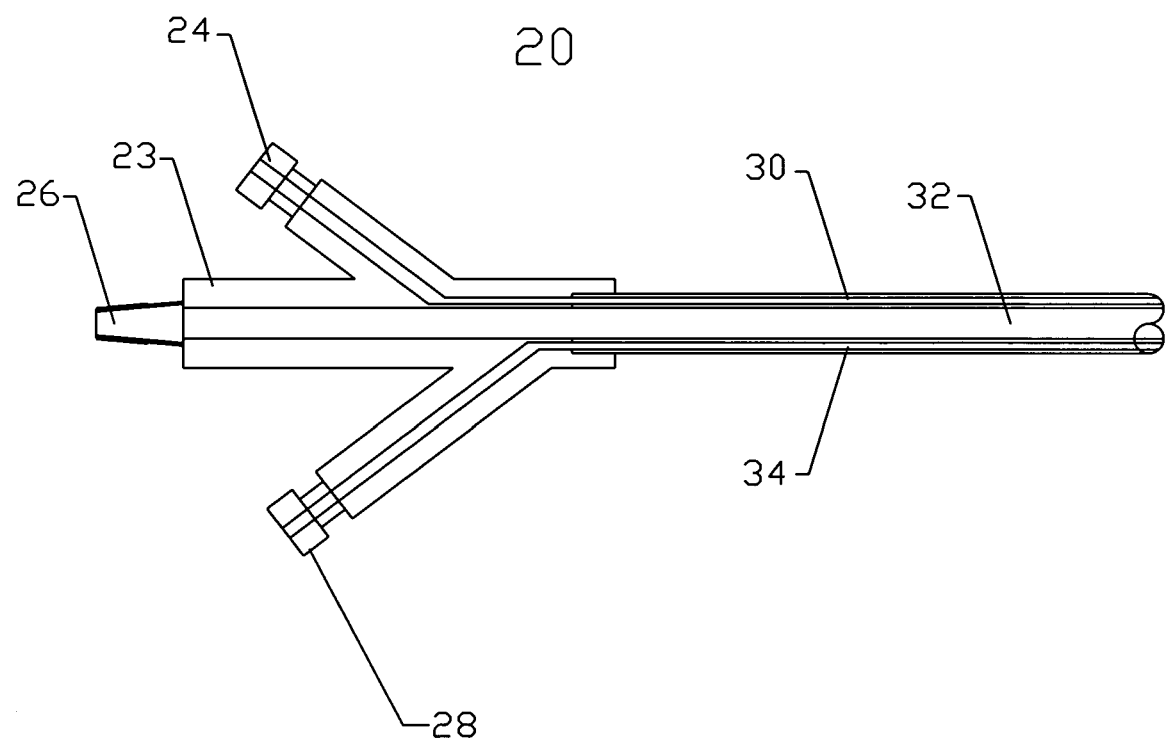
FIG. 4 illustrates, in detail, a longitudinal cross-section of the proximal end of the cannula of FIG. 1 according to aspects of an embodiment of the invention.

FIG. 4 shows the proximal end 20 of the cannula 10 of FIG. 1 in detail. The proximal end 20 is an extension of the connecting tube 22 and comprises the cardioplegic infusion lumen 30, the venous drainage lumen 32, and the inflation lumen 34. The proximal end 20 additionally comprises the manifold 23, which comprises the cardioplegia infusion adapter 24, the venous drainage collection adapter 26 and the balloon inflation adapter 28. The cardioplegia infusion adapter 24 connects to the infusion lumen 30. The venous drainage collection adapter 26 connects to the drainage lumen 32 and the balloon inflation adapter 28 connects to the inflation lumen 34.

Figure 5:
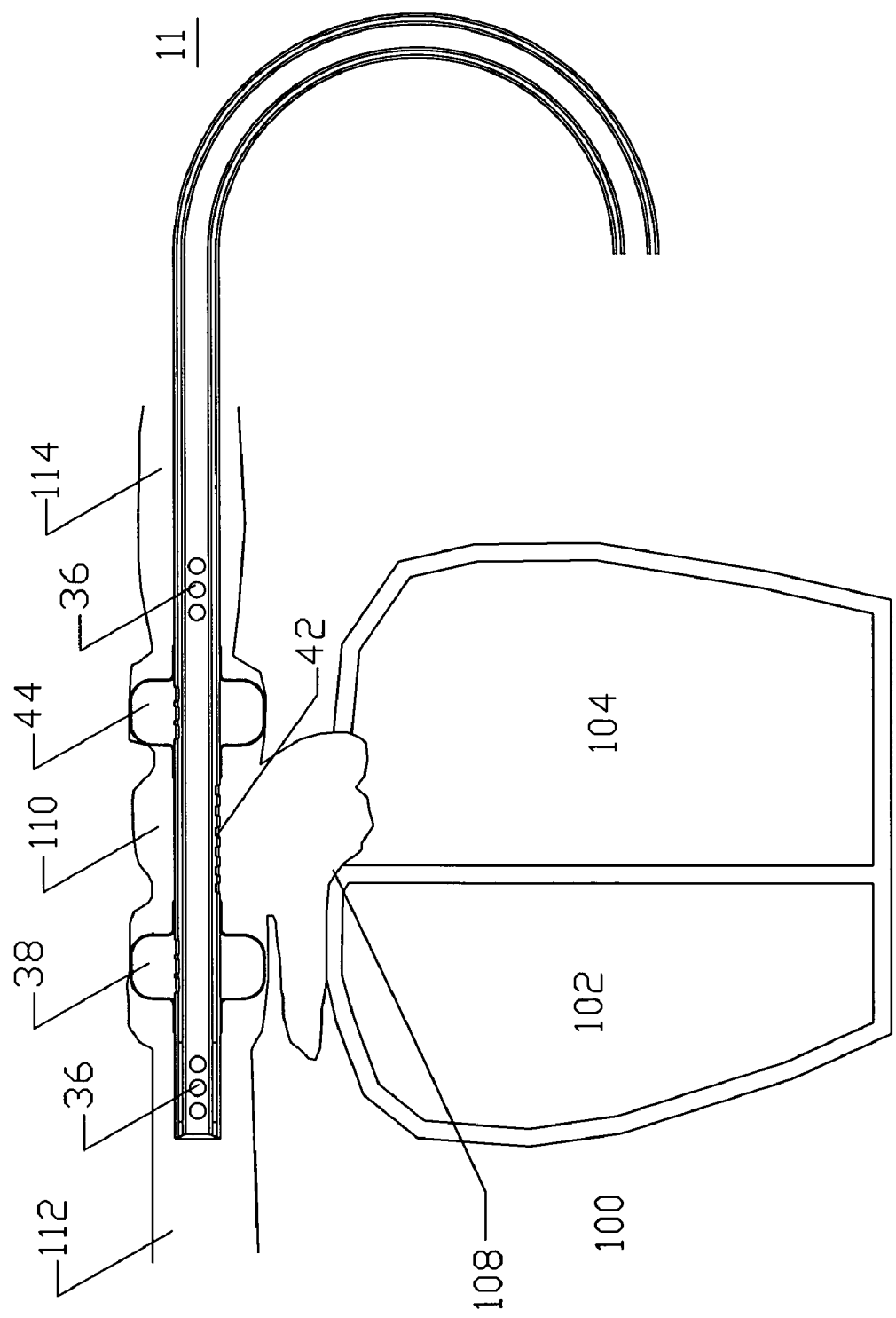
FIG. 5 shows the placement of the cannula of the present invention in the heart for venous drainage and retrograde perfusion according to aspects of an embodiment of the invention.

FIG. 5 illustrates the placement of the cannula 10 of the present invention in a heart 100 during retrograde perfusion. The heart 100 comprises a left ventricle 102, a right ventricle 104, a coronary sinus 108, a right atrium 110, an inferior vena cava 112, and a superior vena cava 114.

During normal operation of the heart, or during the normal cardiac cycle, blood returning from the tissues of the body passes through peripheral veins into the superior 114 and inferior vena cava 112 and into the right atrium 110. The coronary sinus 108 is the region of the heart 100 where blood exits the coronary vascular circuit and passes back into the right atrium 110. The coronary sinus 108 is located in close proximity to the inferior vena cava's entry into the right atrium 110. Blood leaving the coronary circulation by way of the coronary sinus 108 joins the venous blood from the vena cava 112 and 114 in the right atrium 110. The venous blood flows from the right atrium 110 into the right ventricle. Venous blood is pumped by the right ventricle 104 into the lungs where it is oxygenated and where carbon dioxide is removed. The oxygen-rich blood then passes into the left atrium and left ventricle 102 where it is then pumped into the systemic circulation to nourish the organs and tissues of the body. The coronary ostea, or entrance to the coronary arteries, are located at the root of the aorta, just downstream of the aortic valve.

When the heart 100 is placed on cardiopulmonary bypass, blood is removed from the venous circulation at the inferior vena cava 112 and superior vena cava 114 and is routed to an oxygenator that adds oxygen and removes carbon dioxide. The oxygenated blood is pumped back into the patient's systemic circulation so tissues can be perfused while the heart is being surgically repaired.

in an embodiment, the cannula 10 serves the triple function of blocking venous blood from entering the right heart during surgery, removing the venous blood from the vena cava so that it may be extracorporeally oxygenated and pumped back to the patient, and infusing cardioplegia solution into the heart in a retrograde direction during the surgical repair procedure.

Referring to FIGS. 1, 3, 4, and 5, the physician makes an incision in the jugular vein, for example, and inserts the distal tip 18 of the catheter or cannula 10 into the incision. The catheter 10 is threaded into the vein, advanced into the vena cava 112 and 114, and positioned, with the aid of fluoroscopy, for example, such that the balloons 38 and 44 are located in the inferior vena cava 112 and superior vena cava 114, respectively. The cardioplegia infusion ports 42 are located at the entrance to, or inside of, the right atrium 110 and the drainage ports 36 are located in the superior vena cava 114 and inferior vena cava 112, proximal or upstream of the balloons 38 and 44. In one embodiment, the superior and inferior vena cava obstructive balloons 38 and 44 can be adjusted to an appropriate position within the respective vena cava 112 or 114.

Next, the balloon inflation system 16 is activated. Balloon inflation is accomplished by driving balloon inflation fluid from the balloon inflation system 16, through the balloon inflation adapter 28, into the balloon inflation lumen 34, through the balloon inflation ports 40 and 46 and into the balloons 38 and 44. The inflation lumen plug 48 prevents the balloon inflation fluid from escaping from the distal end of the inflation lumen 34. This infusion of balloon inflation fluid causes the balloons 38 and 44 to inflate and occlude the entrance of the right atrium 110 from the superior vena cava 114 and the inferior vena cava 112. Because of this occlusion, blood is prevented from flowing from the superior vena cava 114 and the inferior vena cava 112 into the right atrium 110 of the heart 100, and must exit via the drainage ports 36 of the cannula 10. The blood passes through the cannula 10 and on into the venous reservoir of the cardiopulmonary bypass system, also known as a circuit.

The cardioplegia solution flows from the cardioplegia infusion system 12, through the cardioplegia infusion adapter 24, into the infusion lumen 30, through the cardioplegia infusion ports 42, and into the right atrium 110 where, under a moderate pressure of 120 mm Hg or less, the cardioplegia solution enters the coronary sinus 108 and the right ventricle 104. In order for cardioplegic solution to enter the coronary sinus 108 in a retrograde fashion, the right atrium 110 and ventricle 104 must be pressurized, which necessitates occlusion of the pulmonary artery root. The pulmonary artery thus is typically cross-clamped, for example, to prevent perfusion of the lungs during surgery. The infusion lumen plug 50 prevents the cardioplegia solution from escaping from the distal end of the infusion lumen 30. The cardioplegia solution arrests the beating of the heart 100 by interfering with the sodium potassium cycle of the cardiac muscle cells.

In addition, the venous drainage collection system 14 is activated. Any blood in the superior vena cava 114 and inferior vena cava 112 flows through the drainage ports 36, into the drainage lumen 32, through the drainage collection adapter 26, and into the drainage collection system 14. The drainage collection system 14 collects the venous blood. This blood is, in most cases, routed to a venous reservoir of a cardiopulmonary bypass system. The blood then passes into an oxygenator where it undergoes removal of carbon dioxide and addition of oxygen. The blood also passes through a heat exchanger where it undergoes heat transfer, either heating or cooling. The oxygenated and cooled, or warmed, blood is pumped back into the patient's systemic circulation via an arterial cannula placed in a systemic artery distal to the aortic valve.

The surgeon can now perform the prescribed heart surgery. A single cannula of the present invention provides the infusion, inflation, and drainage functions, which eliminates the need for the multiple cannulae currently used for open-heart procedures.

Figure 6:
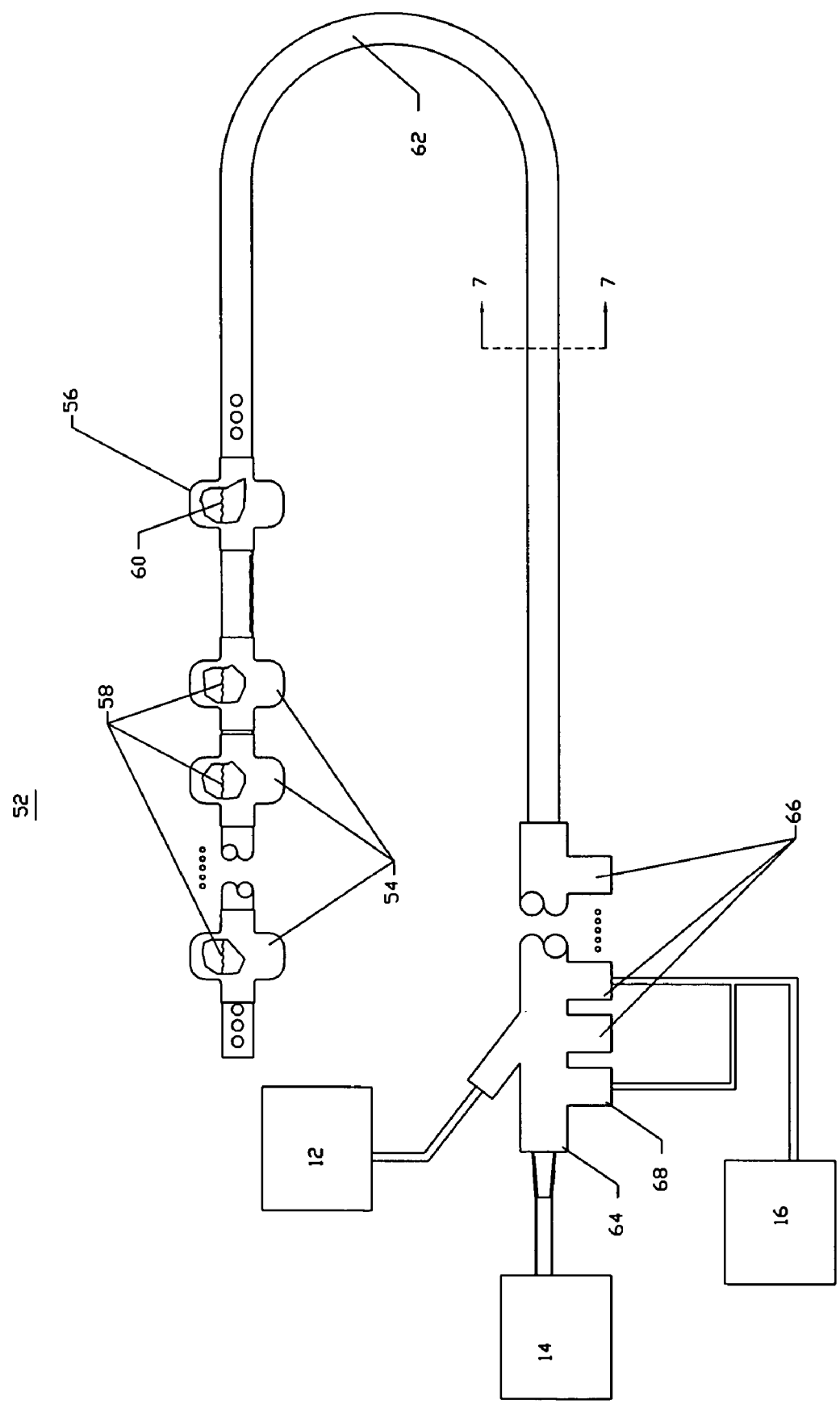
FIG. 6 illustrates, in exterior view, another embodiment of the cannula comprising multiple balloons to accommodate various anatomic differences according to aspects of an embodiment of the invention. Cutouts on the balloons show features on the cannula surface that would normally be hidden by the balloons.

Referring to FIG. 5, patients have different spacing between the entrance of the inferior vena cava 112 into the right atrium 110 and the entrance of the superior vena cava 114 into the right atrium 110. A one-size-fits-all catheter 10 may not be optimum for use in all patients. FIG. 6 shows a more preferred embodiment of the catheter, which compensates for anatomic differences between patients. The operations of cardioplegia infusion and drainage collection are the same as that described earlier for the cannula 10.

Referring to FIG. 6, the catheter or cannula 52 comprises a plurality of first balloons 54, a second balloon 56, a plurality of first balloon inflation port sets 58, a plurality of second balloon inflation ports 60, and a length of connecting tubing 62. The catheter 52 also comprises a manifold 64, which comprises a plurality of first balloon inflation adapters 66 and a second balloon inflation adapter 68. The catheter is connected to the cardioplegia infusion system 12, the venous drainage collection system 14, and the balloon inflation system 16.

Figure 7:
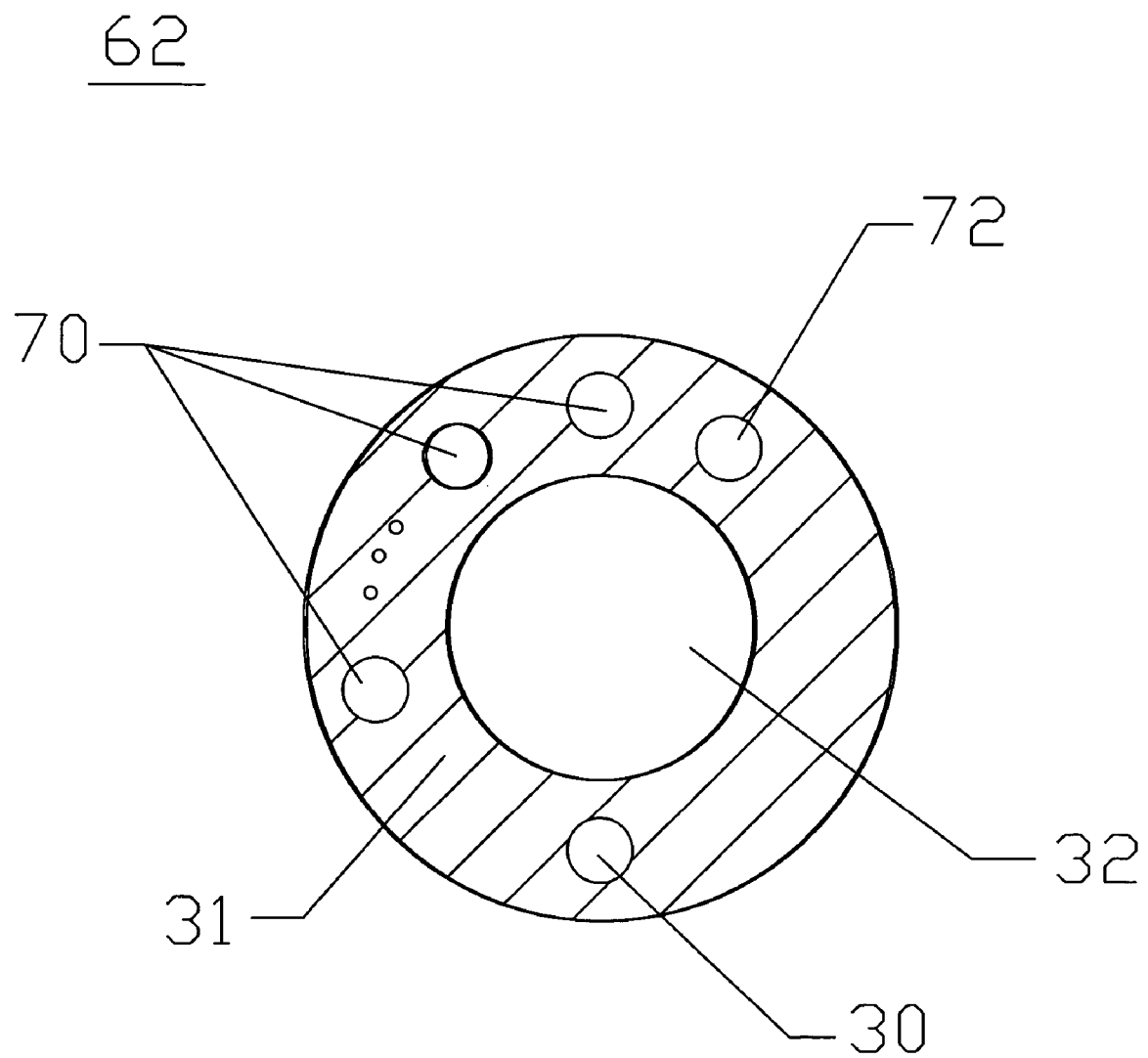
FIG. 7 illustrates a lateral cross-section of a multi-lumen tube for construction of the cannula of FIG. 6 according to aspects of an embodiment of the invention.

FIG. 7 illustrates a cross section of multi-lumen connection tubing 62 for the construction of the catheter 52 of FIG. 6. The tubing 62 comprises a plurality of first balloon inflation lumens 70, a second balloon inflation lumen 72, the infusion lumen 30, the drainage lumen 32, and the wall 31.

Referring to FIGS. 6 and 7, the balloon inflation system 16 connects to the catheter 52 through the first balloon inflation adapters 66 and the second balloon inflation adapter 68. Each first balloon inflation adapter 66 connects to one first balloon inflation lumen 70. The second balloon inflation adapter 68 connects to the second balloon inflation lumen 72. Each set of first balloon inflation ports 58 is located on one first balloon inflation lumen 66. The second balloon inflation ports 60 are located on the second balloon inflation lumen 72. Each first balloon 54 is positioned over one set of first balloon inflation ports 58, such that when inflation fluid is injected through the selected first balloon inflation ports 58, only the first balloon 54 over the selected first balloon inflation ports 58 is inflated. The second balloon 56 is positioned over the second balloon inflation ports 60 such that when balloon inflation fluid is injected through the second balloon inflation ports 60, the second balloon 56 is inflated. Each first balloon inflation adapter 66 has a corresponding first balloon inflation lumen 70, as shown in FIG. 7, a corresponding set of first balloon inflation ports 58, and a corresponding first balloon 54.

Referring to FIGS. 5 and 6, the physician places the catheter 52 into the right atrium 110. The physician places the second balloon 56 in the entrance of the superior vena cava 114 and the series of first balloons 54 line up in the right atrium 110 and into the inferior vena cava 112. The second balloon 56 is inflated to occlude the superior vena cava 114. Only the first balloon 54 in the plurality of first balloons 54, which is in the entrance of the inferior vena cava 112, corresponding to the correct spacing for the patient's heart, is inflated to occlude the inferior vena cava 112. Balloons 54 and 56 to be inflated are connected to the balloon inflation system 16 through their balloon inflation lumen 70 and 72. The balloon inflation lumen 70 of the balloons 54 selected for non-inflation is simply not connected to the balloon inflation system 16. In this manner, the catheter 52 is optimized for the individual patient's anatomy. The better fit minimizes the chance of the balloons 54 and 56 slipping out of position and leaking venous blood into the heart, with potentially severe complications for the surgery patient.

Preferably, the plurality of balloons are located on the distal end of the catheter's cardioplegia infusion ports 42, although multiple balloons proximal to the cardioplegia inflation ports 42 would also be acceptable. Only the balloons that are spaced correctly to occlude the patient's superior 114 and inferior 112 vena cava are inflated.

In another embodiment for multiple balloon inflation selection, a single balloon inflation lumen may be connected to all of the balloons and to a control rod that selectively opens balloon inflation ports to the correct balloon or balloons. Such a control rod would typically be an axially elongate, torqueable structure running the length of the cannula tubing. By rotating or axially moving the control rod by grasping a projection at the proximal end of the cannula, inflation ports would be selectively opened between the balloon inflation lumen and the balloon to be inflated. Markings on the control rod would indicate which balloons were being inflated or which spacing was being chosen. Again, only the balloons correctly spaced to occlude the patient's vena cava are inflated. Other balloons would not be inflated because their ports would not have been selectively opened.

In yet another embodiment of the cannula 10, the distal tip 18 comprises an accordion-like or telescoping structure between the occlusion devices 39 and 45, and a control rod. The accordion-like or telescoping structure allows the length of the cannula 10 to be adjusted so that the occlusion devices 39 and 45 fit the spacing between the patient's superior vena cava 114 and inferior vena cava 112. This accordion-like structure is a longitudinally flexible area of the cannula 10 with corrugations to allow for compression or expansion in length. The control rod extends from the distal tip 18 of the cannula 10 to the proximal end 20. The control rod is linked to the cannula 10 such that pushing or pulling the control rod relative to the proximal end 20 increases or decreases the length of the cannula 10. The control rod is locked into place with a locking device when the correct spacing between the occlusion devices 39 and 45 is achieved. A telescoping structure could be used in place of the accordion-like structure to allow for cannula length adjustment using the control rod.

In yet another embodiment, the balloon inflation adapter 28 is connected to the cardioplegia infusion system 12. In this embodiment, the cardioplegia solution is used in the cardioplegia infusion system 12 to arrest the heart and in the balloon inflation system 16 to inflate the balloons 38 and 44 or 54 and 56. Typically, cardioplegia solution is infused at a pressure of around 20 mmHg. The balloons 38, 44, 54, and 56 may be inflated with an internal pressure of 20 mmHg and this pressure may be derived from the pressure of the cardioplegia solution. This embodiment has the advantage of reduced complexity and simplified pressure limiting.

The balloons 38 and 44 are only one way of occluding the vena cava 112 and 114. Another embodiment of the occlusive structures 39 and 45 comprises one or more external tourniquets. One or more tourniquets may be applied external to the vena cava 112 and 114 to seal the vena cava 112 and 114 to the cannula 10 and prevent cardioplegia solution from escaping the environs of the right atrium entry 110 to the coronary sinus 108.

A further embodiment of the occlusive structures 39 and 45 comprises umbrella mechanisms, which open up to occlude the vena cava. Opening and closing of the umbrellas, optionally with toroidal edge-seal balloons, would be accomplished using a control rod extending along the length of the catheter and out the proximal end of the catheter where it could be grasped.

Figure 8:
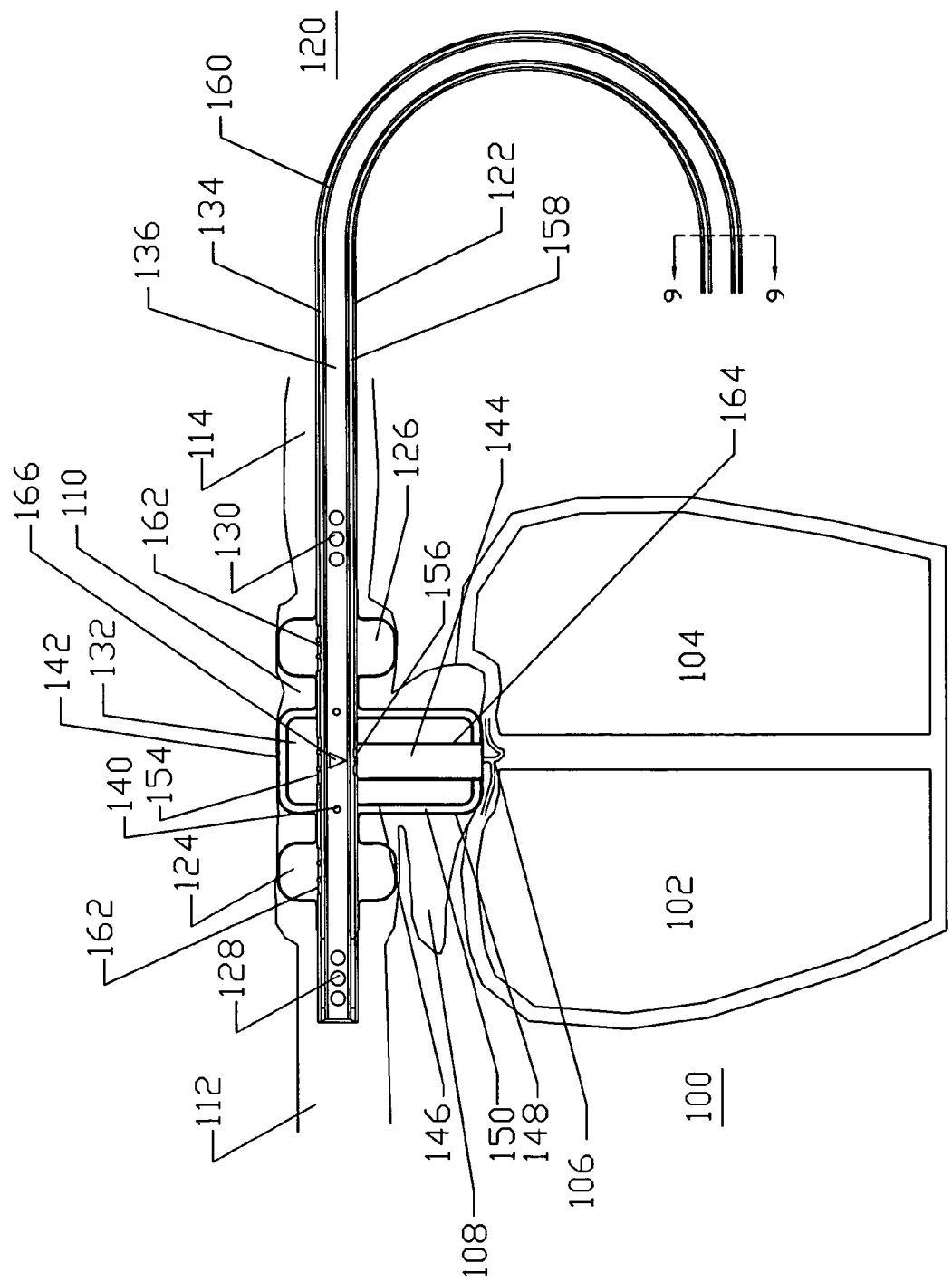
FIG. 8 illustrates a longitudinal cross-section of a cannula comprising a balloon to protect the walls of the vena cava from high pressure during retrograde cardioplegia infusion, according to aspects of an embodiment of the invention.

FIG. 8 illustrates a longitudinal cross-sectional view of the distal end of a catheter or cannula 120 of the present invention, comprising a length of cannula tubing 122, a distal occlusion balloon 124, a proximal occlusion balloon 126, a plurality of distal drainage ports 128, a plurality of proximal drainage ports 130, a protection balloon 132, an occlusion balloon pressurization or inflation lumen 134, a drainage lumen 136, a vacuum lumen 138 (not shown), a plurality of vacuum ports 140, a plurality of protection balloon perforations 142, and a walled-off cardioplegic delivery annulus 144. The protection balloon 132 further comprises an inner protection balloon layer 146, a protection balloon outer layer 148, a vacuum channel 150, one or more occlusion balloon inflation lumens 152, a plurality of protection balloon inflation ports 154, one or more cardioplegia delivery ports 156, and a cardioplegia delivery lumen 158, a protection balloon pressurization or inflation lumen 160, a plurality of occlusion balloon inflation ports 162, a cardioplegia delivery annulus wall 164, and a radiopaque marker 166. FIG. 8 further illustrates the cannula 120 in situ in the heart 100 further comprising the left ventricle 102, the right ventricle 104, a plurality of coronary veins 106, the coronary sinus 108, the right atrium 110, the inferior vena cava 112, and the superior vena cava 114.

Referring to FIG. 8, the protection balloon 132 may be either symmetric or asymmetrically disposed about the length of cannula tubing 122. The protection balloon 132 is sealably affixed to the cannula tubing 122. The protection balloon 132 is affixed to the cannula tubing such that a vacuum channel 150 exists between the inner protection balloon layer and the outer protection balloon layer 148. The vacuum channel 150 is in fluid communication with the vacuum lumen 138 in the cannula tubing 122 by way of vacuum ports 140. The vacuum lumen 138 is in fluid communication with a connector (not shown) on the proximal end of the cannula 120. The walled-off cardioplegic delivery annulus 144 is a feature in the protection balloon 132 that directs cardioplegia from the cardioplegia delivery lumen 158 through cardioplegia delivery ports 156 and on into the coronary sinus. The walled-off cardioplegic delivery annulus 144 is sealed from the rest of the vena cava and right atrium by the protection balloon 132.

A vacuum being drawn through the vacuum channel 150 seals the protection balloon 132 through the protection balloon perforations 142 in the protection balloon outer layer 148. Ridges or indentations (not shown) in the vacuum channel 150 allow the vacuum to be maintained even though the outer protection balloon wall 148 is drawn against the inner protection balloon wall 146 by the vacuum. In this way, pressurized cardioplegia solution can be directed at the coronary sinus 108 and on into the coronary veins 106 without causing excessive pressure on the walls of the right atrium 110 and vena cava 112 and 114. The cardioplegia delivery channel or annulus 144 is directed at and is operably in fluid communication with the coronary sinus. Blood is drained through the drainage lumen 136 by way of the drainage ports 128 and 130 to the proximal end of the cannula 120 where it is routed to a collection device or cardiopulmonary bypass system. As shown in FIG. 8, in a preferred embodiment the protection balloon inflation lumen 160 and the occlusion balloon inflation lumen 134 are the same channel. The protection balloon 132 is inflated by the protection balloon inflation lumen 160 through protection balloon inflation ports 154 while the occlusion balloons 124 and 126 are inflated by the occlusion balloon inflation lumen 134 through the occlusion balloon inflation ports 162. The cardioplegia delivery lumen 158 is preferably asymmetric on the cannula 120 so radiopaque markers 166 are preferred to show the asymmetry and allow correct alignment of the cannula with the heart under fluoroscopy.

Referring to FIG. 8, the cannula tubing 122, comprises an affixed, optional radiopaque marker 166 or plurality of radiopaque markers 122 to allow visibility under fluoroscopy of the position of key elements of the tubing and to delineate the rotational orientation of the tubing 122. The radiopaque (RO) marker 166 is asymmetrically configured circumferentially, in a preferred embodiment, so that under fluoroscopy, the RO marker 166 orientation and the orientation of the tubing 122 can be determined under said fluoroscopic evaluation. Examples of asymmetrical RO markers include, but are not limited to, arrows, rectangles with one rounded side, triangles, and the like. In another embodiment, a plurality of radiopaque markers 166 are asymmetrically arranged to provide the user with cannula tubing 122 rotational information when viewed in two-dimensional projection as is typical with fluoroscopic visualization. An example of a preferred embodiment of multiple radiopaque markers 166 include, but are not limited to two markers 166 that are asymmetric in shape, are located 180-degrees apart on the circumference of the tubing 122 or other cannula structure, such as the protection balloon 132, and each comprises a fenestration or hole that is aligned with a hole on the opposing radiopaque marker 166 to ensure exact rotational orientation of the cannula 120. Such rotational orientation is complimentary to the longitudinal or axial positioning or orientation of the cannula 120.

Figure 9:
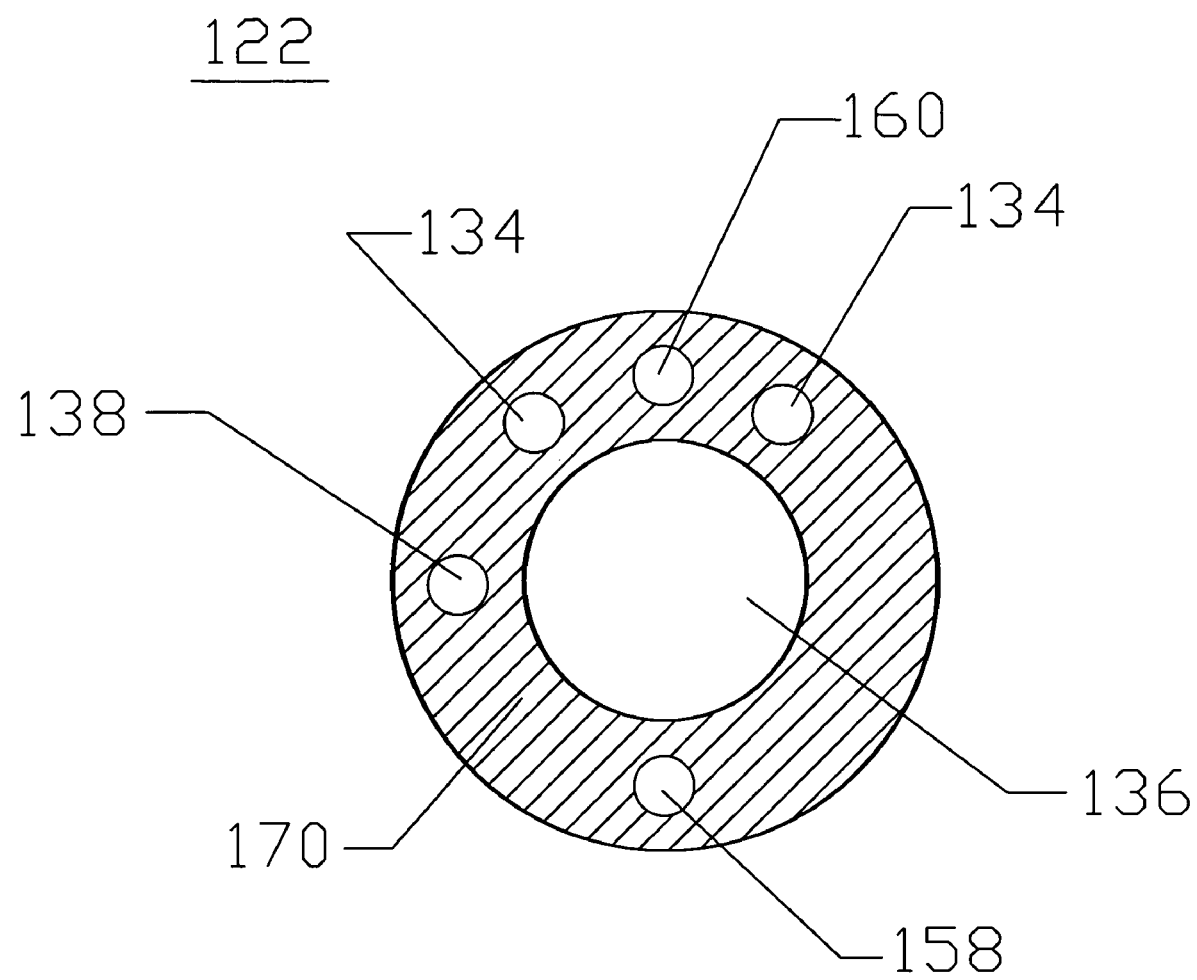
FIG. 9 illustrates a lateral cross-section of an axially elongate, multi-lumen tube for use in a cannula comprising a balloon to protect the walls of the vena cava from high pressure during retrograde cardioplegia infusion, according to aspects of an embodiment of the invention.

FIG. 9 illustrates a lateral cross section of a length of cannula tubing 122. The cannula tubing comprises a tube wall 170, a vacuum lumen 138, a drainage lumen 136, one or more occlusion balloon inflation lumens 134, a cardioplegia delivery or infusion lumen 158, and a protection balloon inflation lumen 160.

Referring to FIGS. 8 and 9, the cannula tubing 122 is preferably flexible but has column strength and torqueability. The cannula tubing 122 diameter ranges from 5 mm to 20 mm. Preferably the cannula tubing 122 diameter ranges from 8 mm to 15 mm. The cannula tubing 122 is preferably fabricated by extrusion. The cannula tubing 122 may also be fabricated by winding a wire or polymer coil or a wire or polymer braid around a mandrel. The cannula tubing 122 may be poured or dipped or extruded over this braid or coil to provide additional torqueability, kink-resistance, and the like. The cannula tubing 122 is typically fabricated from polymers such as, but not limited to, PEBAX, polyurethane, silicone, poly vinyl chloride, polyethylene, polypropylene, polyimide, polyamide, and the like. The braid or coil used to reinforce the cannula tubing 122 is preferably fabricated from wire such as, but not limited to, round or rectangular cross-sections of stainless steel, nitinol, Kevlar, polyimide, polyester, and the like. The radiopaque markers 166 may be comprised of metals such as platinum, tantalum, gold, and the like or they may be additives of barium sulfate and the like, formed as attached rings, extruded stripes, or other shapes.

Figure 10:
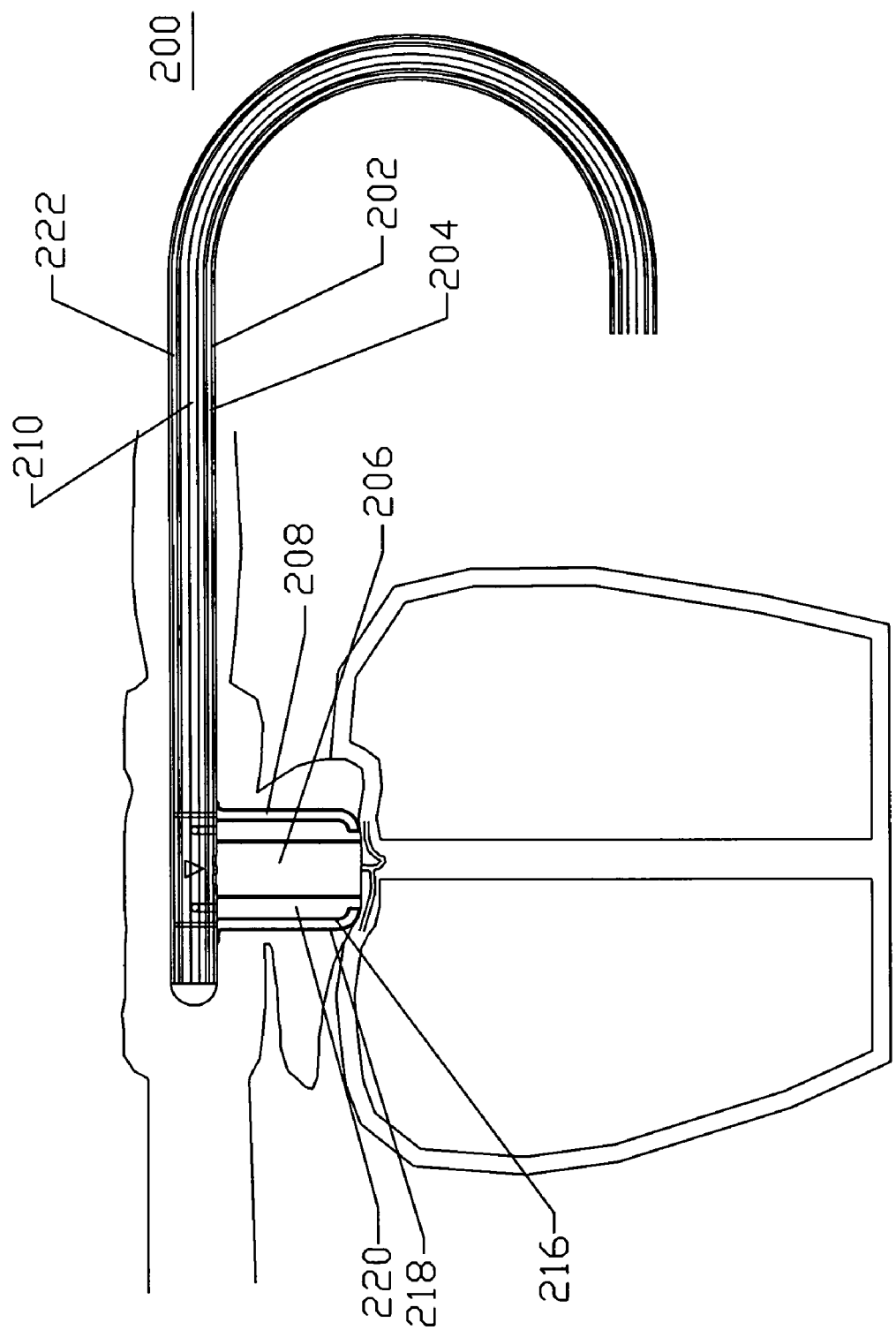
FIG. 10 illustrates a longitudinal cross-section of the distal end of a cannula comprising a laterally directed retrograde cardioplegia delivery annulus and a seal system surrounding the cardioplegia delivery annulus, according to aspects of an embodiment of the invention.

FIG. 10 shows yet another embodiment of a venous cannula 200 adapted for retrograde administration of cardioplegia solution to a heart during cardiopulmonary bypass. The venous cannula 200 comprises a length of multi-lumen tubing 202 with a proximal end and a distal end, a cardioplegia solution infusion lumen 204, a cardioplegia solution infusion annulus 206 affixed at or near the distal end of the cannula 200, an annular seal ring 208 affixed to the distal end of the cannula 200 surrounding the cardioplegia solution infusion annulus 206, a vacuum lumen 210 operably connected to the vacuum or sealing annulus 220 of the annular seal ring 208, a cardioplegia solution infusion port 212 (not shown) affixed at the proximal end of the cannula 200, and a vacuum port 214 (not shown) affixed at the proximal end of the cannula 200. The annular seal ring 208 of the cannula 200 further comprises an optional inner wall 216, an outer wall 218, and a sealing annulus 220. The cannula 200 further comprises an optional inflation lumen 222 and an inflation port 224 (not shown), which are affixed to each other and operably connected to the sealing annulus 220. The outer wall of the cardioplegia solution infusion annulus 206 is, in one embodiment, the same as the inner wall of the sealing annulus 220. Webs or attachments (not shown) connect the inner wall of the sealing annulus 220 to the outer wall 218 of the annular seal ring 208 but permit application of a vacuum to tissue where the sealing annulus 220 touches said tissue. Expansion or movement of the outer wall 218 moves the inner wall of the sealing annulus 220 correspondingly.

Referring to FIG. 10, the cardioplegia solution infusion port 212 comprises an attachment to a cardioplegia infusion system, which preferably comprises a reservoir of cardioplegia solution and a pump. The annular seal ring 208 comprises the inner wall 216 and the outer wall 218 and the sealing annulus 220. The annular seal ring 208 controllably seals to the right atrial wall around the coronary sinus by way of a vacuum drawn through the vacuum lumen 210 by way of the vacuum port 214. The annular seal ring 208, when attached to the atrial wall by vacuum, prevents or minimizes the escape of cardioplegia solution from the cardioplegia solution infusion annulus 206 into the right atrium. In a preferred embodiment, the annular seal ring 208 is an expandable structure that can be inserted endovascularly and routed to the right atrium. The annular seal ring 208 is then expanded and placed against the tissue surrounding the coronary sinus. The interior most lumen of the annular seal ring 208 is the cardioplegia solution infusion annulus 206. Such expansion of the annular seal ring 208 is, in one embodiment, accomplished by providing an inflation lumen 222 within the tubing 202 and an inflation port 224 at the proximal end of the tubing 202, the inflation port 224 operably connects to the inflation lumen 222. Pressurized fluid such as air, saline, or radiopaque liquid is infused under pressure and inflates the annular seal ring, which consists of multiple walls. A vacuum is then drawn through the vacuum lumen 210 as described earlier while cardioplegia solution is infused into the coronary sinus through the cannula 200 via a retrograde approach. In one embodiment, the cannula 200 further comprises the integral venous drainage system shown in FIG. 8. In another embodiment, the cannula 200 does not require a venous drainage system. The materials and methods used for manufacture of this embodiment, are the same as or similar to those used to manufacture the cannula of FIG. 8.

In one embodiment, the annular seal ring 208 and the cardioplegia solution infusion annulus 206 are affixed to the cannula tubing 202 substantially at a direction perpendicular to the longitudinal axis of the cannula tubing 202. Thus, the annular seal ring 208 projects sideways, or is laterally directed, and toward the coronary sinus while the main axis of the cannula 200 is longitudinally located within the vena cavae. In a preferred embodiment, the annular seal ring 208 and cardioplegia solution infusion annulus 208 are controllably extendable in the direction lateral to the longitudinal axis of the cannula tubing 202. The expansion may be controlled from the proximal end of the cannula 200 by way of pull wires running through lumens in the tubing 202 or by inflation of balloon structures through inflation lumens in the tubing 202.

Figure 11:
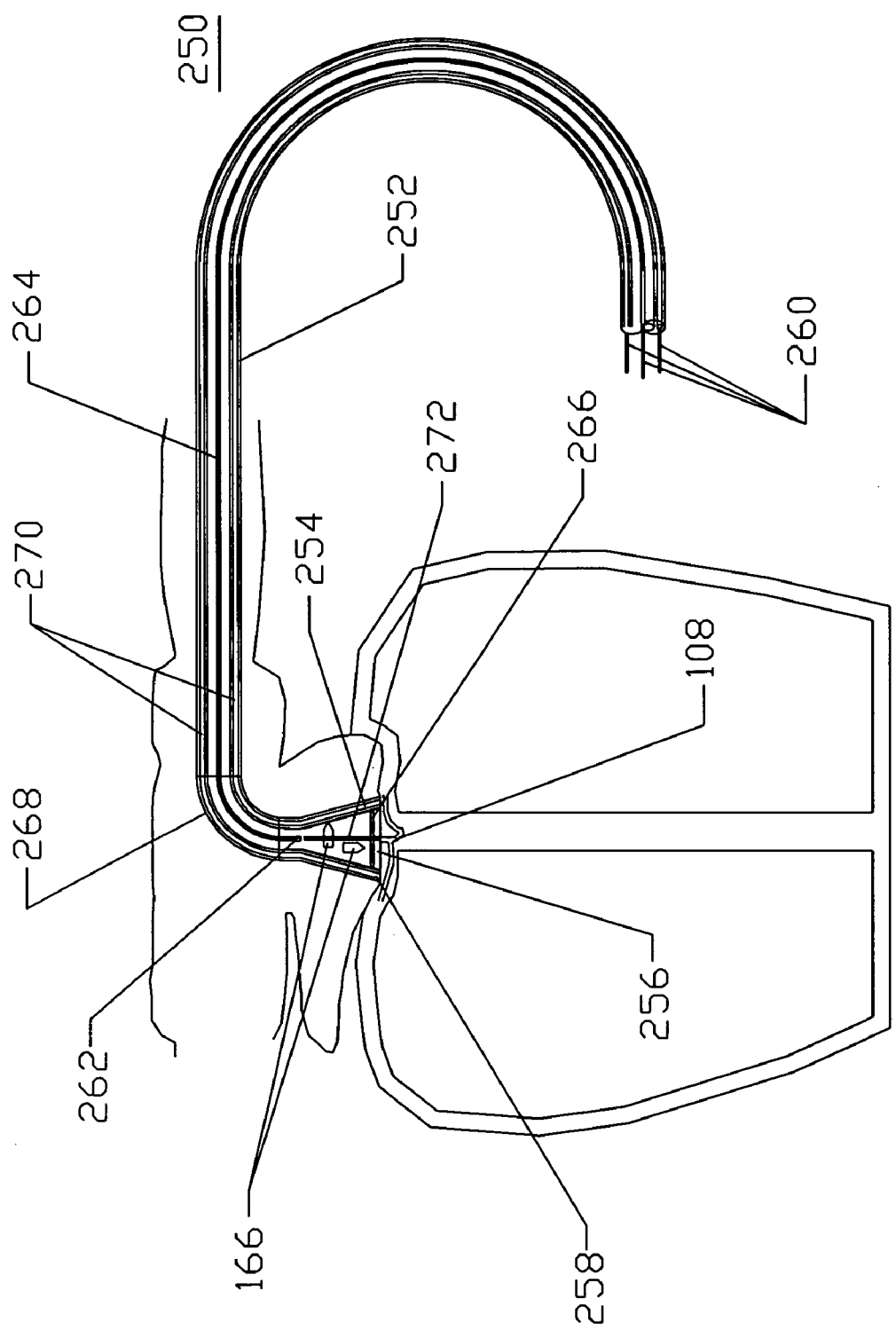
FIG. 11 illustrates a longitudinal cross-section of a distal end of a cannula comprising a forward directed retrograde cardioplegia delivery annulus, a seal system surrounding the cardioplegia delivery annulus, and a steering mechanism, according to aspects of an embodiment of the invention.

FIG. 11 illustrates another embodiment of the cannula 250, wherein the annular seal ring 258 and the cardioplegia infusion annulus 256 are disposed concentrically with the axis of the tubing 252 so that the distal tip of the cannula 250 opens to form the cardioplegia solution infusion annulus 256. In this embodiment, steering apparatus is disposed within the cannula 250 to bend, steer, or articulate the distal end of the cannula tubing 252 and allow the annular seal ring 258 to be mated or docked with the tissue surrounding the coronary sinus 108. The steering apparatus comprises, in one embodiment, one or more pull-wires 260 slidably disposed within lumens 264 in the tubing 252. The pull-wire lumens 264 are preferably located at 90-degree or 120-degree interval spacing about the cannula tubing 252. For clarity, FIG. 11 shows only one pull-wire lumen 264. The pull-wire 260 associated with the illustrated pull-wire lumen 264 is also shown exiting the cannula tubing 260 cutaway. Additional pull-wires 260, whose pull-wire lumens 264 are not shown, are shown exiting the tubing 252 cutaway more proximally. The pull-wires 260 are terminated at the proximal end of the cannula 250 with grips or knobs (not shown) that allow manual or power-assisted tension to be applied to the pull-wires. The pull-wires 260 are terminated and affixed at the distal tip of the cannula 250 into attachment points 262 on the distal end of the tubing 252. The pull-wires 260 are preferably disposed on opposite circumferential sides of the tubing 252 so that tension on one pull-wire 260 causes the tubing 252 to bend to that side on which the pull-wire 260 is located. A minimum of one pull-wire 260 is required but more pull-wires 260 are desirable. In a preferred embodiment, three or more pull-wires 260 are comprised by the cannula 250 to provide full X-Y orientation and articulation. The pull-wires 260 are fabricated from polyimide, polyester, stainless steel, nitinol, or other material with suitable tensile strength and biocompatibility. The pull-wire 260 may be either monofilament or multifilament with a braided structure. The pull-wire 260 may further be coated with polytetrafluoroethylene or other fluoropolymers to minimize friction. In yet another embodiment, the pull-wire 260 is shape-memory nitinol and is selectively or controllably heated by application of electrical energy across its length to achieve contraction of the pull-wires 260. Such electrical energy is applied to electrical leads (not shown) that run longitudinally through the cannula tubing 252 from the proximal end to the distal end and can provide a complete circuit to any component comprised by the cannula 250.

Referring to FIG. 11, in one embodiment, the tubing 252 is more flexible in a region 262 just proximal to the distal tip of the cannula 250. This region of increased flexibility 268 allows the cannula tubing 252 to bend preferentially at that flexible region 268 upon application of tension in the pull-wires 260. In yet another embodiment, the steering apparatus comprises microactuators such as those fabricated from shape memory metals and Ohmic heating elements or from electromechanical actuators. Exemplary shape-memory microactuators include those described in U.S. Pat. No. 6,447,478 to Ronald Maynard, entitled Thin-Film Shape Memory Alloy Actuators and Processing Methods, the entirety of which is included herein by reference. Electrical energy, provided at the proximal end of the cannula 250 and transmitted by electrical cabling within lumens in the tubing 252, provide the power and control for the microactuators. The control unit, which supplies the electrical energy to the microactuators minimally comprises a power supply and an on-off switch for each microactuator. The control unit may, in other embodiments, comprise computer systems or other types of logic circuitry to control the power to the microactuators. The microactuators are preferably affixed longitudinally across the area of increased flexibility near the distal end of the cannula 250 and are disposed on opposing sides of the tubing to provide counter-motion since these actuators generally only work in tension, not expansion.

Referring to FIG. 11, the lateral cross-sectional shape of the annular seal ring 258 is generally or substantially circular but may be oval or any other appropriate shape. The annular seal ring 258 is, in a preferred embodiment, a double wall structure that permits a vacuum to be applied to a vacuum annulus 254 between the walls to hold the annular seal ring 258 against the cardiac tissue with a high level of force. Vacuum is drawn at the proximal end of the cannula 250 and is transmitted to the vacuum annulus 254 by way of vacuum lumens in the cannula tubing 252 which are operably connected to the vacuum annulus 254 and the applied vacuum at the proximal end of the cannula 250. The cardioplegia infusion annulus 256 is a region interior to the inner wall of the annular seal ring 258, which further permits and guides the infusion of cardioplegia solution, in a non-cannulating fashion, to the coronary sinus 108. In one embodiment, the annular seal ring 258 is of constant, non-tapering cross-section. In a preferred embodiment, the annular seal ring 258 comprises an elastomeric wall and an inflatable or expandable structure 266 at the distal tip to provide for diametric or radial expansion to a size greater than that of the cannula 250. In one embodiment, the expandable structure 266 comprises a ring of shape-memory nitinol that expands under application of electricity which results in Ohmic heating of the nitinol to a temperature above its austenite finish temperature ($A_f$). The nitinol expandable ring 266 may be a simple split ring or it may be a pattern of diamonds, "W" s or "Z" s or other typical cardiovascular stent shapes known in the art that are capable of diametric expansion. The cannula 250 may further comprise a plurality of slats or longitudinal elastomeric elements 272, which serve as a strain relief and permit smooth tapering of the tip when the expandable ring 266 is activated. These separated longitudinal elastomeric elements 272 are fabricated from stainless steel, nitinol, polyester, cobalt nickel alloys or other materials with high strength in the form of leaf springs. In a preferred embodiment, the longitudinal elastomeric elements 272 are fabricated from shape-memory nitinol and, upon application of electrical energy, are heated to above their austenitic finish temperature and expand to a pre-determined shape. In all embodiments, electrical energy is supplied at the proximal end of the cannula 250 and is routed to the distal tip of the cannula 250 by electrical leads (not shown) longitudinally disposed within lumens or co-extruded within the tubing 252. These electrical leads are electrically connected to both ends of the nitinol itself or to high resistance heating elements disposed in proximity of the shape-memory nitinol. Removal of the electrical energy results in cooling and restoration of the non-expanded configuration of the longitudinal elastomeric elements 272. In another embodiment, the annular seal ring 258 further comprises an expandable structure 266, which is a toroidal or annular balloon that expands under pressure applied at the proximal end of the cannula 250 and transmitted through the length of the cannula tubing 252 by a pressurization lumen to the balloon, the interior of which is in fluid communication with the pressurization lumen. The balloon may be either an elastomeric balloon or an inelastic angioplasty type balloon and is pressurized with water, saline, radiopaque contrast media, gas, or other material. The annular seal ring 258 preferably has a smooth distal edge that is capable of sealing to cardiac tissue without causing damage or trauma. Radiopaque markers 166 are, in a preferred embodiment, affixed to the distal end of the cannula 250 to assist with visualization and orientation of the cannula 250 distal tip under fluoroscopy. The radiopaque markers 166 are fabricated from material such as, but not limited to, platinum, gold, iridium, tantalum, and the like.

The device or apparatus for such retrograde cardioplegia delivery is directed to a method for retrograde delivery of cardioplegia without cannulating the coronary sinus. Embodiments of the apparatus of the present invention permit the entire coronary sinus and coronary venous circuit to be perfused, and therefore, both the right and left coronary veins are perfused. Referring to FIG. 11, perfusion is, in a preferred embodiment, performed by sealing the catheter around the entrance to the coronary sinus 108 but not inserting a catheter into the coronary sinus 108. In one embodiment, the preferred method comprises inserting a catheter into the right atrium and inflating a protection balloon, which seals to the region around the coronary sinus. The protection balloon prevents high-pressure cardioplegia solution from over-inflating the right atrium or surrounding structures. Once the catheter or cannula seals to the region around the coronary sinus, any air or gas is removed from the perfusion lumen and infusion of cardioplegic solution is initiated. At the conclusion of the procedure, cardioplegia solution infusion terminates, the vacuum terminates, and the surgeon, robot, or operator withdraws the cannula from the patient with any access sites being sealed by appropriate surgical, least invasive, or minimally invasive techniques.

The catheter, cannula, device, or apparatus, all of which are used herein interchangeably, further comprises a cardioplegia delivery channel that is oriented toward the coronary sinus and sealed against the tissue around the coronary sinus. Such guiding or orientation is done either under direct visualization or by fluoroscopic, MRI, or ultrasonic guidance. Fluoroscopic orientation and guidance is accomplished by visualizing radiopaque markers or structures on the catheter. The radiopaque markers or structures permit evaluation of orientation of the cannula since they are, in a preferred embodiment, asymmetrically placed about the cannula. The step of sealing is performed by drawing a vacuum on the protection device or balloon to pull surrounding tissue against the balloon or protection device, thus sealing the region around the coronary sinus. In another embodiment, the sealing is performed by inflating a sealing structure into the right atrium or by opening an umbrella-type structure, optionally comprising an inflatable toroidal edge sealing balloon, to occlude and seal off parts of the right atrium. Cardioplegia solution is then infused into the coronary sinus through infusion ports on the cannula. With this method, the use of occluding balloons is optional and may not be needed since the protection balloon seals the coronary sinus from the rest of the circulation. Venous drainage is optionally performed by the same cannula as that used for the cardioplegia delivery and the drainage ports are preferably positioned within the superior and inferior vena cava. In another embodiment, cardioplegia is infused through a catheter that is inserted into the coronary sinus 108, but which is perforated so that cardioplegia solution can flow into the coronary veins 106 of both the right heart and the left heart. This system does not cannulate the coronary sinus 108 at the region of the coronary veins 106. In yet another embodiment, the cannula is inserted surgically into the right atrium through an opening in the right atrium or vena cava, rather than being routed endovascularly to the right atrium from a remote access site.

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A system adapted for retrograde administration of cardioplegia solution to a heart of a patient during cardiopulmonary bypass comprising:
   an axially elongate cardioplegia delivery cannula comprising a proximal end, a distal end, a cardioplegia delivery lumen, an inflation lumen, and a vacuum lumen;
   wherein the lumens are oriented with their longitudinal axes parallel to a longitudinal axis of the cannula;
   a reservoir of cardioplegia solution external to the patient and comprising an outlet port;
   a cardioplegia solution infusion mechanism comprising a proximal end, a distal end, an inlet port affixed to the proximal end of the mechanism, and an outlet port affixed to the distal end of the mechanism;
   wherein the inlet port of the mechanism is operably connected to the outlet port of the reservoir and wherein the outlet port of the mechanism is operably connected to the proximal end of the cardioplegia delivery cannula;
   wherein the cardioplegia solution infusion mechanism receives cardioplegia solution and routes pressurized cardioplegia solution into the cardioplegia delivery lumen;
   a cardioplegia outlet port operably connected to the distal end of the cardioplegia delivery lumen, wherein the cardioplegia outlet port is configured to be located within a right atrium of the heart and proximate to a coronary sinus, without cannulating the coronary sinus; and
   a protection device affixed to the cannula near the distal end of the cannula comprising a balloon operably connected to the inflation lumen, and an annular seal ring affixed to the balloon and operably connected to the vacuum lumen;
   wherein the balloon is configured to be inflated against the interior of the right atrium of the heart and the inflated balloon forms an open channel between the cardioplegia outlet port and the coronary sinus, such that the annular seal ring contacts the right atrium and a vacuum pulled through the vacuum lumen causes the tissue of the right atrium to be drawn against the annular seal ring;
   wherein the annular seal ring is maintained in position by the inflated balloon; and
   wherein the protection device limits pressurization of the right atrium by the pressurized cardioplegia solution.

2. The cannula of claim 1 further comprising at least one radiopaque marker to permit positioning of the cannula under fluoroscopy.

3. The cannula of claim 2 wherein the radiopaque markers are asymmetrical and provide rotational positioning information when viewed under fluoroscopy.

4. The cannula of claim 1, wherein said cardioplegia solution infusion mechanism comprises a pump and a length of axially elongate tubing.

5. The cannula of claim 1 wherein the annular seal ring comprises an inner and an outer wall and a vacuum channel.

6. The cannula of claim 1 wherein the protection device comprises a cardioplegia delivery channel.

7. The cannula of claim 1 wherein the protection device comprises perforations in an outer wall of the annular seal ring that enables a vacuum to form between the protection device and tissues of the right atrium.

8. The cannula of claim 1 wherein the protection device comprises ridges to prevent collapse of the protection device under a vacuum.

9. The cannula of claim 1 wherein said protection device is an expandable structure that becomes rigid upon full expansion.

10. The cannula of claim 1, wherein said cardioplegia solution infusion mechanism comprises a flexible cardioplegia reservoir, a pressure cuff disposed around the flexible cardioplegia reservoir and configured to generate inward force on the flexible cardioplegia reservoir to generate pressure within the cardioplegia solution contained therein, and a length of axially elongate tubing further comprising an infusion lumen.

11. A method of cannulating a patient's heart during cardiopulmonary bypass comprising:
   inserting a cannula into a venous system of a patient;
   positioning the cannula so that said cannula enters a right atrium of the heart;
   inflating a protection balloon within the right atrium, wherein the protection balloon comprises an outer wall, an inner wall, a pressurization channel operably connected to the region inside the inner wall of the protection balloon, a vacuum channel operably connected to the region between the outer wall and the inner wall, and perforations in the outer wall of the balloon;
   withdrawing a vacuum within an annulus formed between the outer wall and the inner wall of the balloon, wherein the vacuum attaches the protection balloon to the atrial wall to prevent atrial wall overexpansion; and;
   infusing cardioplegia solution, in the retrograde direction, into a coronary sinus of the heart, without cannulating the coronary sinus, wherein the cardioplegia solution is infused through a cardioplegia solution infusion annulus into the coronary sinus, further wherein the vacuum holds the protection balloon against the atrial wall such that the escape of cardioplegia solution from the cardioplegia solution infusion annulus into regions other than the coronary sinus is prevented or minimized.

12. The method of claim 11 further comprising orienting the protection balloon so that a cardioplegia delivery channel is directed at, is in fluid communication with, and creates a seal around, the coronary sinus.

13. The method of claim 11 wherein infusing cardioplegia solution does not over-pressurize the right atrium.

14. The method of claim 11 wherein positioning the cannula comprises visualizing a radiopaque marker, affixed to the cannula, under fluoroscopy.

15. The method of claim 11 wherein infusing cardioplegia solution further comprises sealing a cardioplegia delivery channel to a right atrial wall so as to block the escape of cardioplegia solution into the right atrium.

16. A venous cannula adapted for retrograde administration of cardioplegia solution to a coronary sinus of a heart during cardiopulmonary bypass comprising:
- a length of axially elongate multi-lumen tubing with a proximal end and a distal end, and comprising a cardioplegia solution infusion lumen, a balloon inflation lumen, and a vacuum lumen;
- a cardioplegia solution infusion annulus located near the distal end of the multi-lumen tubing and operably connected to the cardioplegia solution infusion lumen;
- a sealing balloon, operably connected to the balloon inflation lumen, configured to be inflated within a right atrium of a heart such that the exterior of the sealing balloon comes into substantial contact with the tissue of the right atrium of the heart, wherein the sealing balloon comprises an outer wall, an inner wall, and a pressurization channel operably connected to the region inside the inner wall of the sealing balloon;
- an annular seal ring comprising a plurality of exit ports of a vacuum channel operably connected to the region between the outer wall and the inner wall of the sealing balloon, wherein the annular seal ring is radially disposed on the periphery of the sealing balloon, and is configured to be driven against the tissue of the right atrium of the heart by inflation of the sealing balloon, further wherein the sealing balloon is configured to surround the cardioplegia solution infusion annulus, and wherein the vacuum lumen is operably connected to the vacuum channel;
- a cardioplegia solution infusion mechanism, wherein the cardioplegia solution infusion mechanism receives cardioplegia solution from an external cardioplegia solution source and delivers the cardioplegia solution under pressure to the cardioplegia solution infusion lumen; and
- wherein the coronary sinus is not cannulated during the retrograde perfusion.

17. The venous cannula of claim 16, wherein said annular seal ring comprises an inner and an outer wall and a sealing annulus and wherein said annular seal ring controllably seals to the right atrial wall around the coronary sinus by way of a vacuum and prevents the escape of pressurized cardioplegia solution from the cardioplegia solution infusion annulus into the right atrium.

18. The venous cannula of claim 16 further comprising radiopaque markers to permit positioning and visualization under fluoroscopy.

19. The venous cannula of claim 16 wherein all components are fabricated from biocompatible materials.

* * * * *